United States Patent [19]

Maganias

[11] Patent Number: 4,473,083
[45] Date of Patent: Sep. 25, 1984

[54] DEVICE AND METHOD FOR ALLERGY TESTING

[76] Inventor: Nicholas H. Maganias, Reston Medical Bldg., 1712 Club House Rd., Reston, Va. 22090

[21] Appl. No.: 330,587

[22] Filed: Dec. 14, 1981

[51] Int. Cl.³ .............................................. A61B 5/00
[52] U.S. Cl. ..................................... 128/743; 604/46; 604/47
[58] Field of Search ..................... 128/743; 604/46, 47

[56] References Cited

U.S. PATENT DOCUMENTS

| | | | |
|---|---|---|---|
| Re. 25,637 | 9/1964 | Kravitz et al. | 604/47 |
| 2,190,745 | 2/1940 | Vollmer | 128/743 |
| 3,072,122 | 1/1963 | Rosenthal | 604/46 |
| 3,515,126 | 6/1970 | Fregert | 128/743 |
| 3,814,097 | 6/1974 | Ganderton et al. | 604/304 |

*Primary Examiner*—Kyle L. Howell
*Assistant Examiner*—Christine A. Fukushima
*Attorney, Agent, or Firm*—Cushman, Darby & Cushman

[57] ABSTRACT

A method for allergy testing is carried out by applying to the skin of a patient a thin, flexible strip of adhesive tape a portion of which carries on its adhesive side at least one group of closely spaced projecting lances carrying an allergen, so that the tape releasably adheres to the skin, pressing at least the lance-carrying portion against the skin to cause the lances to penetrate the skin to a depth less than the subcutaneous tissue thereby carrying the allergen into the skin, and maintaining contact between the allergen and the thus-traumatized skin cells, leaving the strip in place for a period of time sufficient for the patient's skin, if allergic to the allergen, to produce an allergic reaction; and removing the strip from the skin whereby the patient's allergy to the allergen may be determined by visual observation of the skin area penetrated by the lances.

12 Claims, 3 Drawing Figures

DEVICE AND METHOD FOR ALLERGY TESTING

This invention relates to a method and device for allergy testing the skin of a patient.

BACKGROUND

Testing the skin of a patient for an allergic reaction to any of a variety of allergens is a known technique involving penetration of the allergen into a small area of the skin and subsequently visually observing the reaction, if any, of the skin to the allergen. Known procedures for applying the allergen include the scratch test, the prick test and the intradermal test. The scratch test is carried out by applying a few drops of the allergen to the skin and slightly abrading the skin by scratching at that location. The prick test is similar excpet that abrasion of the skin is effected by making a plurality of pricks with a sharp needle. The intradermal test is carried out by injecting the allergen into the skin.

United States patents relating to the introduction of biochemical substances into the skin include Krug et al No. 3,289,670; Kravitz et al No. Re. 25,637, Nos. 2,817,336, 3,062,212, 3,136,314 and 3,351,059; Wager et al No. 2,893,392, Ganderton et al No. 3,814,097 and Gerstel et al No. 3,964,482.

SUMMARY OF THE INVENTION

The present invention is based in part on the observation that each of the scratch test, the prick test and the intradermal test has one or more disadvantages. The scratch test may not produce enough scarification of the skin and thus lead to an inaccurate conclusion due to insufficient skin cell damage to permit adequate entry of and reaction with the allergen. The prick test may produce excessive trauma, for example, microbleeding, which can produce histamine release thereby confusing the results of the test. With the intradermal test it is frequently difficult to titrate the degree of skin reaction and large and often false positive reactions develop. Each procedure has its own advantages, however. The medical practitioner will generally decide on which procedure to use taking into consideration the time required for the test, pain inflicted on the patient, trauma to the skin, weak reactions, expense and other features.

The present invention provides an allergy testing method, and a disposable device for use in carrying out the method, which combines a number of the advantages of the usual procedures while avoiding or reducing the disadvantages referred to above. The method involves applying to the skin of the patient a test strip in the form of a thin flexible piece of adhesive tape a portion of which carries on its adhesive side at least one group of closely spaced projecting lances coated with the allergen. The test strip, and in particular the portion carrying the lances, is then pressed against the skin to cause the lances to penetrate the skin to a depth less than the subcutaneous tissue thereby carrying some of the allergen into the skin and maintaining constant contact between the allergen and the traumatized skin cells. After a period of time appropriate for the skin to react with the allergen, for example 15 to 20 minutes, the test strip including the lances is removed from the skin and discarded. The degree of skin reaction, in terms of inflammation, swelling or the formation of protuberances, and hence the degree of allergy is then determined by the medical practitioner by visually observing the area of skin which was punctured by the lances. Several such tapes, each carrying a different allergen, can be applied to the skin simultaneously or essentially simultaneously. Alternatively a single tape can carry a plurality of groups of lances, each group carrying a different allergen. The appearance of the skin area may be compared to one or more control skin areas which have been similarly punctured by similar test strips having lances free of allergen.

The test strip for carrying out the method comprises a flexible strip of adhesive tape carrying on a portion of its adhesive surface at least one group of closely-spaced short lances which project from the tape, the allergen being carried by the lances. The lances may be made of plastic or metal. The group of lances is preferably circular and has a diameter less than the smallest dimension of the adhesive surface of the strip. A suitable arrangement is 5 to 10 lances disposed in a circular group of approximately ⅛ inch diameter. The length of the lances may be in the range 1/16 inch to 1/32 inch. The preferred shape of the strip is rectangular, somewhat smaller than the conventional adhesive bandage applied to minor cuts and scratches, although square, circular, oblong or other shapes are satisfactory. It has been found that test strips of this kind when used as described above do not produce excessive trauma or microbleeding, while at the same time they produce reliable test results due in part to the fact that they maintain constant contact between the allergen and the traumatized skin cells during the test.

The allergen initially applied to the lances may be in liquid form or solid form. If liquid, it is preferably impregnated into and retained in the interstices between the lances. If dry, distilled water may be added shortly before use to dissolve or disperse the allergen and allow impregnation. In either case the lances may be covered with a removable protective cover to exclude air and dust and to maintain the lances in sterile condition until ready for use. The cover may be a plastic film overlying the lances only or overlying the lances and the layer of adhesive. The allergen may of course be any allergen, such as those typically used for testing allergy to trees, grasses, weeds, cat hair, dog epithelium, house dust, molds, spores and certain inhalants.

The lances may be held in their relative positions by having their inner ends secured to a substrate which in turn is attached to the adhesive tape. The substrate may be flexible or rigid and may be attached to the adhesive tape by means of the same layer of adhesive which adheres the tape to the patient's skin. Preferably the substrate is slightly concave outwardly so as to provide a cavity for retaining the liquid allergen.

For the convenience of the medical practitioner the allergy testing strips can be supplied in kit form, with each strip being marked to identify its respective allergen or allergens. The kit may also include control strips having no allergen applied to their lances. Use of the strips by the practitioner is convenient, as no instruments are required and as the strips are discarded after use.

Figure 2:
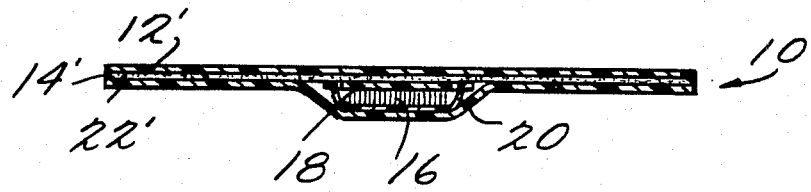
FIG. 2 is a sectional view taken on the line 2—2 of FIG. 1.
Figure 3:
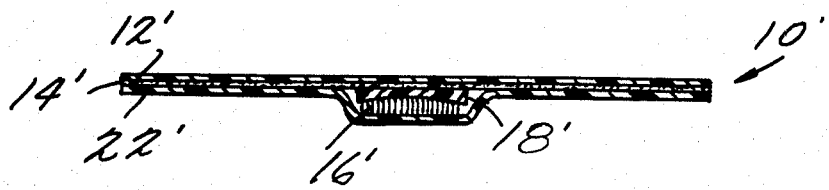
FIG. 3 is a sectional view similar to FIG. 2 illustrating a second embodiment of a test strip.

The thickness of the layers in FIGS. 2 and 3 is exaggerated for clarity of illustration.

DETAILED DESCRIPTION

Figure 1:
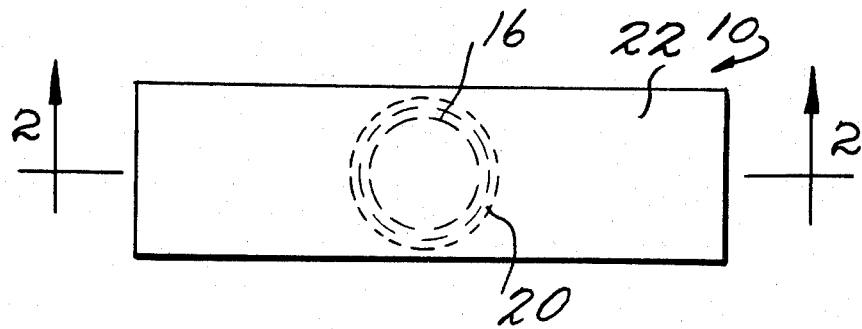
FIG. 1 is a bottom view of a test strip embodying the principles of the present invention.

FIGS. 1 and 2 illustrate an allergy test strip 10 which includes a strip of flexible adhesive tape, which may be conventional, in the form of a plastic strip 12 having on one surface a layer of pressure-sensitive adhesive 14. Projecting from the adhesive surface is a group of pointed or bladed lances 16 which carry an allergen (not illustrated) on their surfaces and/or in the interstices between them. The inner ends of the lances 16 are attached to a substrate 18 which in turn is attached to the film 12 by means of the adhesive layer 14. Preferably the substrate 18 is relatively rigid compared to the adhesive tape, although it can be flexible. A removable protective cover 20 overlies the group of lances 16 and is sealed in place at its periphery by contact with the adhesive layer 14. The cover 20 could alternatively by relatively rigid or elastic and held in place by frictional engagement with the periphery of the group of lances. A removable protective film 22 overlies the cover 18 and the exposed adhesive and is held in place by the latter. In the illustrated embodiment the test strip 10 is rectangular and the group of lances is circular, these being the preferred shapes.

FIG. 3 illustrates a similar allergy testing strip 10' which differs somewhat from the FIG. 1 device. In the FIG. 3 embodiment, the relatively rigid substrate 18' is concave outwardly to form a cavity or well for retaining liquid allergen. Also, there is a single removable film 22' which overlies both the group of lances and the exposed adhesive layer 14'.

To use the test strip 10 or 10' the medical practitioner first removes the protective elements 22, 20 or 22'. If the allergen is in liquid form no further preparation is required. If the allergen is in dry form the practitioner will apply several drops of sterile water to the group of lances 16 or 16' to dissolve or disperse the allergen and allow it to impregnate the spaces between the lances. After sterilizing the skin portion selected for the allergy test, the practitioner applies the adhesive side of the test strip 10 or 10' to the skin to hold the strip in place. Simultaneously or subsequently he gently and firmly presses with his fingers against the strip opposite the group of lances to cause the latter to penetrate the skin. The liquid allergen is thus carried partly into the skin and is maintained in constant contact with the traumatized skin cells until the strip is removed. A contact time of 15-20 minutes is generally suitable and upon removal of the strip the practitioner observes the punctured skin area to determine the extent of allergic reaction. The punctured skin area can be compared to an adjacent control area which has been punctured by the allergen-free lances of a control test strip.

What is claimed is:

1. A method for allergy testing comprising: applying to the skin of a patient a thin, flexible strip of adhesive tape a portion of which carries on its adhesive side a lance device having at least one projecting lance which carries an allergen, so that the tape releasably adheres to the skin, the lance device including a substrate having a concave surface facing in a direction away from the strip of adhesive tape to provide a cavity for retaining liquid allergen, said at least one lance projecting from said concave surface; pressing said strip and lance device against the skin to cause the lance to penetrate the skin to a depth less than the subcutaneous tissue thereby carrying a portion of the allergen into the skin and maintaining contact between the allergen and the thus-traumatized skin cells; in a similar manner applying and pressing against the skin of the patient a control strip and lance device of generally the same construction but without allergen associated with the lance; leaving both strips and lance devices in place for a period of time sufficient for the patient's skin, if allergic to the allergen, to produce an allergic reaction; and removing both strips and lance devices from the skin whereby the patient's allergy to the allergen may be determined by visual comparison of the two skin areas penetrated by the lances.

2. A method as in claim 1 wherein the lance device includes at least one group of closely spaced lances projecting from the concave surface, said method including retaining allergen in the interstices between the lances.

3. A method for allergy testing comprising: applying to the skin of a patient a thin, flexible strip of adhesive tape a portion of which carries on its adhesive side a lance device having at least one projecting lance which carries allergen, so that the tape releasably adheres to the skin, the lance device including a substrate having a concave surface facing in a direction away from the strip of adhesive tape to provide a cavity for retaining liquid allergen, said at least one lance projecting from said concave surface; pressing said strip and lance device against the skin to cause said strip to releasably adhere to the skin and to cause said projecting lance to penetrate the skin to a depth less than the subcutaneous tissue thereby carrying the allergen into the skin and maintaining contact between the allergen and the thus-traumatized skin cells, leaving the strip in place for a period of time sufficient for the patient's skin, if allergic to the allergen, to produce an allergic reaction; and removing the strip and lance device from the skin whereby the patient's allergy to the allergen may be determined by visual observation of the skin area penetrated by the lances.

4. A method as in claim 3 wherein the lance device includes at least one group of closely spaced lances projecting from the concave surface, said method including retaining allergen in the interstices between the lances.

5. A method as in claim 1 or 3 wherein a plurality of the allergen-carrying test strips are applied to the patient's skin generally simultaneously, each such strip carrying a different allergen.

6. A test strip for allergy testing comprising a flexible strip of tape having one of its surfaces coated with an adhesive; a portion of said one surface carrying a lance device having a substrate from which projects at least one lance, said lance carrying an allergen, and said substrate having a concave cavity facing in a direction away from the strip of adhesive tape to provide a cavity for retaining liquid allergen, said at least one lance projecting from said cavity.

7. A test strip as in claim 6 wherein at least one group of closely spaced lances project from said substrate.

8. A test strip as in claim 7 wherein said lances are disposed in a circular group with the cavity.

9. A test strip as in claim 8 wherein the allergen is in the form of a body of liquid retained within the cavity and within the interstices between the lances.

10. A test strip as in claim 6 including a removable protective cover overlying said at least one lance.

11. A lance device for use in allergy testing by a technique involving penetration of an allergen into the skin comprising a rigid substrate having an imperforate concave surface forming a cavity in the substrate for retaining a quantity of liquid allergen and at least one lance projecting from said concave surface and extending to a location outside the cavity for penetrating the skin and carrying liquid allergen into the skin when the device is pressed against the skin.

12. A method for allergy testing comprising applying to the skin of a patient a lance device which comprises a rigid substrate having an imperforate concave surface forming a cavity in the substrate retaining a liquid allergen and at least one lance projecting from said concave surface and extending to a location outside the cavity, pressing the lance device against the skin to cause the projecting lance to penetrate the skin to a depth less than the subcutaneous tissue thereby carrying the allergen into the skin and maintaining contact between the allergen and the thus-traumatized skin cells, leaving the lance device in place for a period of time sufficient for the patient's skin, if allergic to the allergen, to produce an allergic reaction whereby the patient's allergy to the allergen may be determined by visual observation of the skin area penetrated by the lance.

* * * * *